United States Patent [19]

Ishida et al.

[11] 4,247,541

[45] Jan. 27, 1981

[54] KS-2-B

[75] Inventors: Nakao Ishida, Sendai; Hiroshi Maeda, Kumamoto; Fujio Suzuki, Sendai; Toshikatsu Fujii, Yokohama; Ituro Mizutani, Numazu, all of Japan

[73] Assignee: Kirin Brewery Company Limited, Tokyo, Japan

[21] Appl. No.: 38,263

[22] Filed: May 11, 1979

[30] Foreign Application Priority Data

May 12, 1978 [JP] Japan ................................. 53-55460

[51] Int. Cl.³ ............................................ A61K 35/00
[52] U.S. Cl. ..................................... 424/116; 435/171
[58] Field of Search ........................ 424/116; 195/81; 435/171

[56] References Cited

U.S. PATENT DOCUMENTS 3,454,696  7/1969  Weinstein et al. ................. 424/116

Primary Examiner—Jerome D. Goldberg
Attorney, Agent, or Firm—Browdy and Neimark

[57] ABSTRACT

KS-2-B was obtained as purified material from the culture of *Daedalea dickinsii* KSDD 6 (FERM-P No. 3993), *Lentinus edodes* KSLE 7 (FERM-P No. 3994) or *Lentinus edodes* KSLE 28 (FERM-P No. 4196). This substance, KS-2-B, is an effective interferon inducing substance.

4 Claims, 5 Drawing Figures

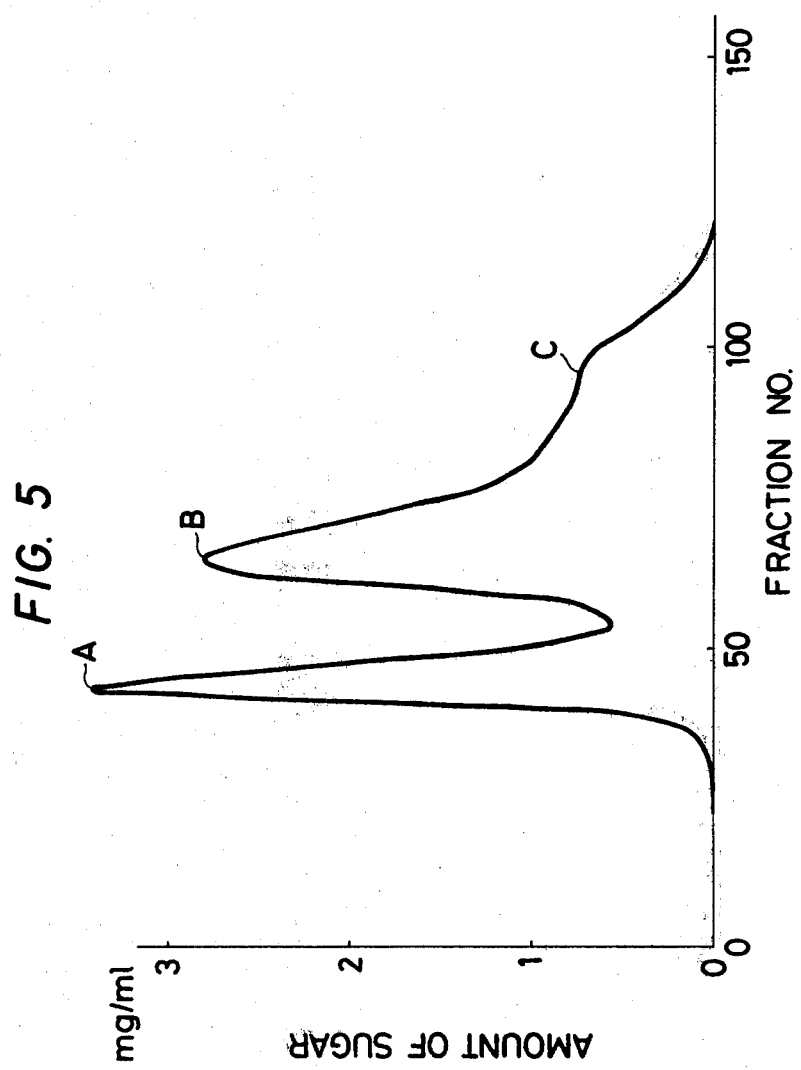

KS-2-B

This invention relates to a novel substance, KS-2-B. More particularly, this invention is concerned with the novel substance, KS-2-B, which is capable of potentiating immunological function, of inducing interferon and of stimulating macrophage and other cellular functions. As a consequence its administration results in remarkable antiviral effects in the host animals.

KS-2-B according to the present invention can be obtained by purifying the culture of *Daedalea dickinsii* KSDD 6 (FERM-P No. 3993), *Lentinus edodes* KSLE 7 (FERM-P No. 3994), or *Lentinus edodes* KSLE 28 (FERM-P No. 4196). KS-2-B thus obtained are found to be capable of inducing the body's production of interferon.

The above cultures have been deposited and made a part of the culture collection of the Fermentation Research Institute, Agency of Industrial Science and Technology, Ministry of International Trade and Industry, Japan, where these were given the above accession numbers and they are available to the public upon request.

Thus, the present invention has been completed.

BRIEF EXPLANATION OF THE DRAWINGS

FIG. 5 indicates an elution pattern of Sephadex G-100 column wherein peak A represents KS-2-B, and peaks B and C represent impurities.

Figure 1:
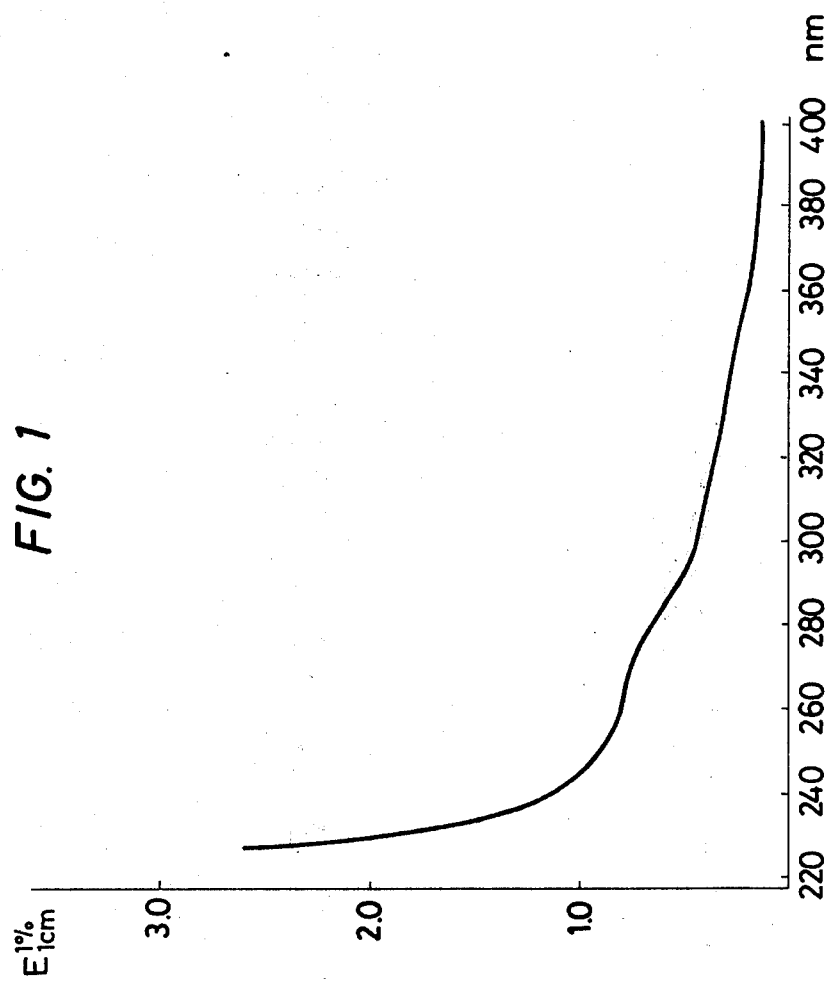
FIG. 1 shows ultraviolet absorption spectrum of KS-2-B.
Figure 2:
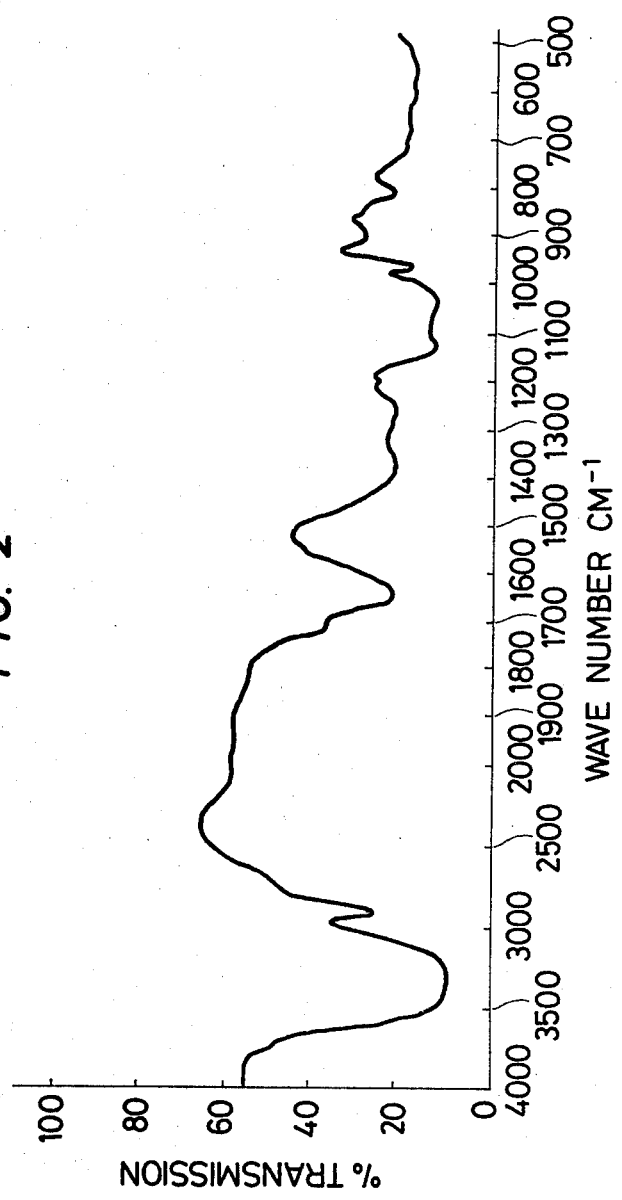
FIG. 2 shows infrared absorption spectrum of KS-2-B.
Figure 3:
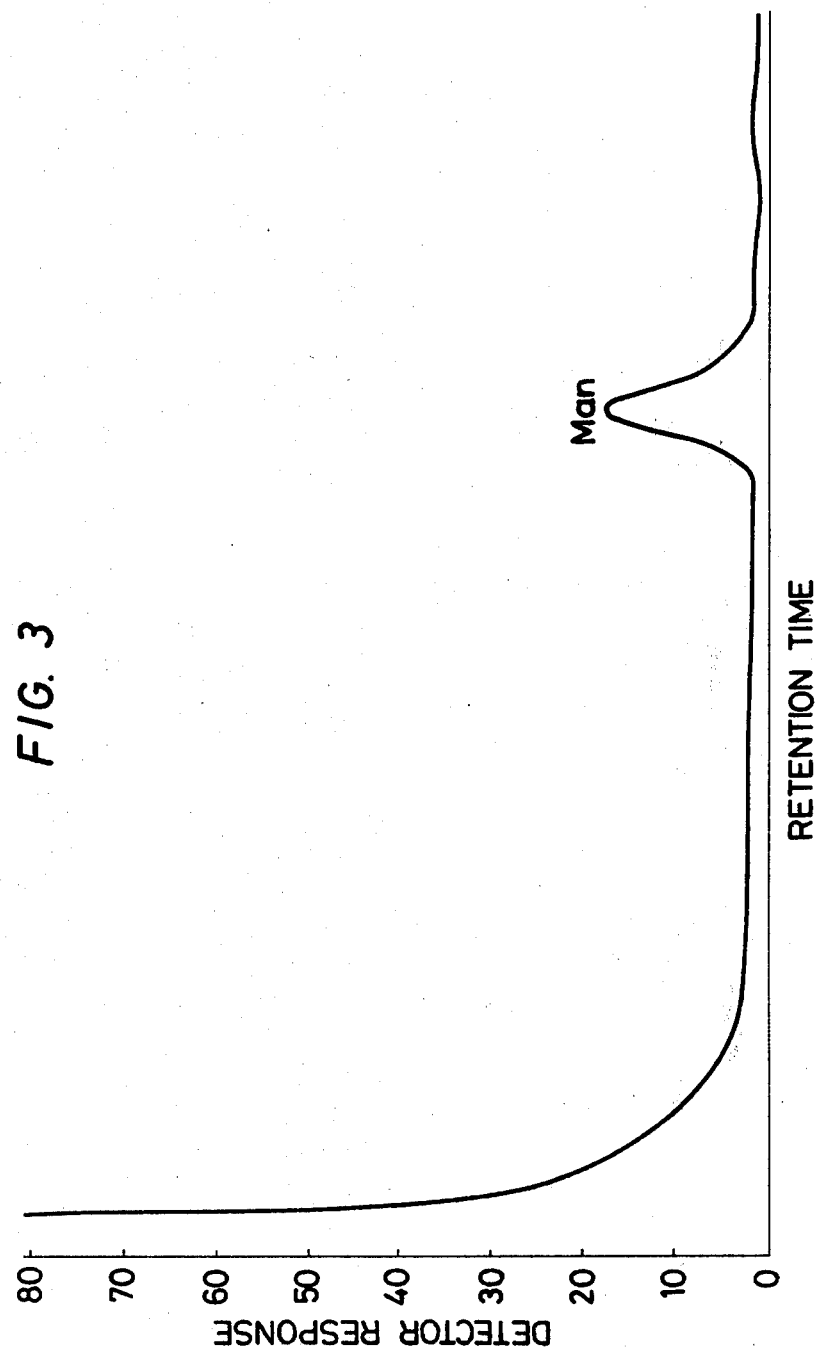
FIG. 3 shows sugar composition analysis by gas-liquid chromatography after acid hydrolysis.

The physicochemical properties of KS-2-B are described in detail as follows:

1. Elemental analysis: C: 43.98% H: 6.77% N: 1.37% Ash: trace.
2. Molecular weight: 75,000±15,000 (by ultrafiltration method using membrane filters, PM-10, XM-50, XM-100A, made by Amicon Co., Lexington, Mass., and appropriate polysaccharide as reference standard).
3. Appearance: White amorphous powder.
4. Decomposition point: Approx. 185° C. (based upon measurement of the browning temperature by capillary method using "Silicone Oil WF-30").
5. UV Spectrum: The spectrum is shown in FIG. 1.
6. IR spectrum: The spectrum is shown in FIG. 2.
7. pH: 5.92. (in aqueous solution).
8. Solubility: Soluble in water, insoluble in organic solvents such as ethanol, acetone, n-hexane, n-butanol, phenol and so forth.
9. Specific optical rotation: $[\alpha]_D^{25} = +61.8°$ (0.788% aqueous solution)
10. Homogeneity: a. Equilibrium density gradient centrifugation (with CsCl 120,000 g×72 hours, CsCl): single peak. b. Electrophoresis on cellulose acetate membrane: single spot. c. Gel filtration (Sephadex G-100): single peak by rechromatography.
11. Specific gravity: $\rho = 1.623$ (by equilibrium density gradient centrifugation with CsCl, 120,000 g×72 hours,)
12. Color reaction:
Phenol-$H_2SO_4$ reaction: positive
Anthrone reaction: positive
Molisch's reaction: positive
Elson-Morgan reaction: negative
Carbazole-$H_2SO_4$ reaction: positive
Folin-Ciocarteau reaction: positive
Biuret reation: positive
Toluidine blue O staining: negative
Ninhydrin reaction: positive 13. Sugar composition: KS-2-B was subjected to acid hydrolysis, followed by alditolation and acetylation. The sugar composition was determined by gas-liquid chromatography. The results are shown in FIG. 3. The sugar composition of this substance is almost mannose.

14. Amino acid composition: KS-2-B, 8.0 mg, was sealed in a Pyrex ampoule in vacuo together with 1.1 ml of distilled 6 N HCl, and subjected to acid hydrolysis at 110° C. for 24 hours. After removal of HCl, amino acid analysis was performed with a Nihon Denshi 6 AH amino acid analyser. The total amount of recovered amino acids was about 14.52 μmoles/mole of KS-2-B (based on a molecular weight of 80,000). The amino acid composition of this substance is mainly serine, threonine and alanine, and minutely glutamic acid, valine, proline, aspartic acid, glycine and isoleucine. Furthermore, although other amino acids are found in a very small quantity from time to time, histidine, arginine, cystine and methionine are absent in KS-2-B. No correction for decomposition was counted in the data.

15. Linkage of mannan in KS-2-B: KS-2-B, 5 mg, was dissolved in 1 ml of 0.2 M citrate-phosphate buffer (pH 4.0, containing 0.5 M NaCl), and 5 milliunit of α-mannosidase (derived from Turbo cornutus), obtained from Seikagaku Kogyo Co., Ltd., Tokyo, was added to the above solution.

The mixture was placed in the dialysis tube (about 1 cm in diameter×5 cm long, Code No. 8×100, Union Carbide Inc., Chicago Ill.) which was immersed in 30 ml of said buffer contained in a test tube (2.5 cm×20 cm). The reaction was carried out at 27°±2° C. under reciprocal shaking (120 Hz).

Figure 4:
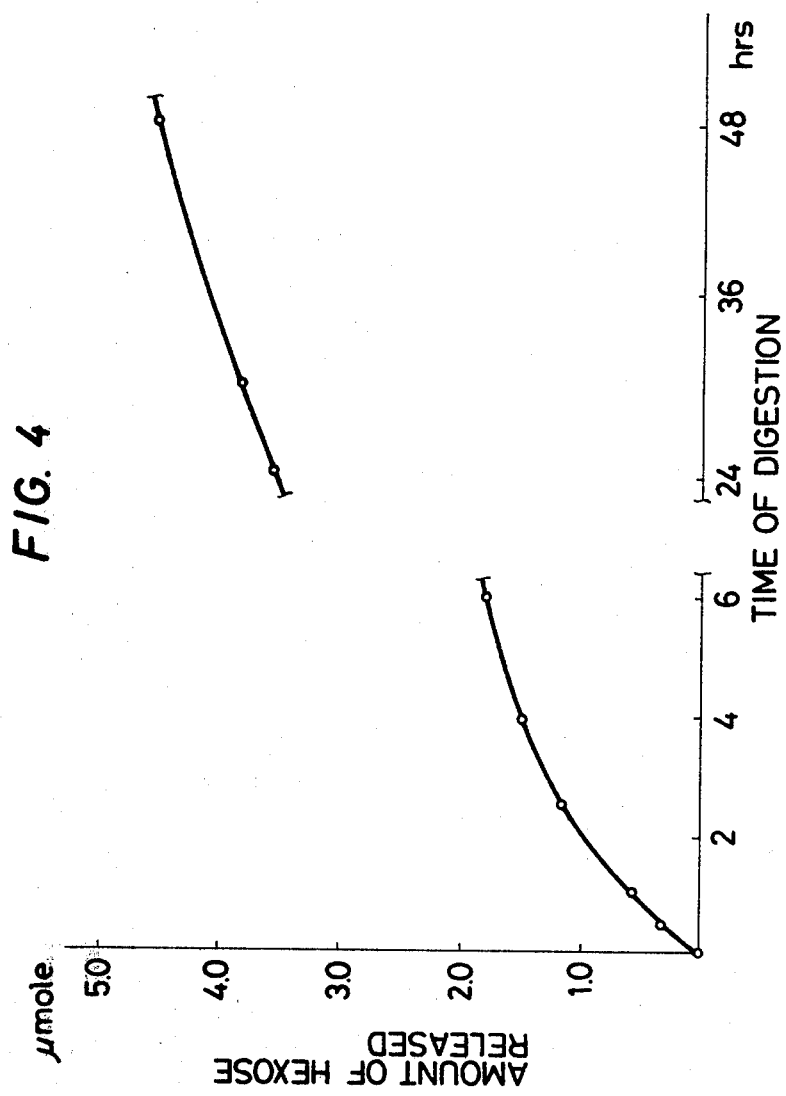
FIG. 4 is time course of mannose liberation from KS-2-B during α-mannosidase treatment.

Mannose, liberated from mannan containing α-linkage at the non-reducing terminal by the action of α-mannosidase, is dialyzed into the external solution. During the course of enzyme reaction, an aliquot of the external solution is withdrawn at various time intervals and subjected to mannose analysis by phenol-$H_2SO_4$ method. The results are shown in FIG. 4.

The residual weight of KS-2-B after α-mannosidase digestion corresponded to about 66.3% of the initial weight. The total amount of mannose liberated into the external solution for a period of 48 hours was about 5 μmoles (correspond to about 25% of the initial amount of KS-2-B) per 5 mg of KS-2-B, assuming the molecular weight of KS-2-B is $8 \times 10^4$.

Thus, it became clear that mannose was linked by α-linkage (α-mannose) in KS-2-B. However, the existence of other types of linkages is not clear. In addition, the sugar percolation has not been detected in the control experiment without the enzyme. From above results, KS-2-B is estimated to contain an α-linked mannan.

The important biological characteristic of this substance lies in that it potentiates an immunological function of the animal, and also man. When the present substance is given to a host animal, interferon is induced in its serum to increase the interference titer and macrophage in the animal is activated. Furthermore, it has become clear that the administration of KS-2-B is highly effective against infections caused by pathogenic bacteria and viruses.

From these results, it became clear that KS-2-B has a capability of enhancement of the host defense function.

The present substance is produced by culturing the mycelium of microorganisms. Such microorganisms are exemplified by the followings: *Lentinus edodes* KSLE 28 (FERM-P No. 4196), *Daedalea dickinsii* KSDD 6 (FERM-P No. 3993), *Lentinus edodes* KSLE 7 (FERM-P No. 3994) and so forth.

As the culture medium, any general medium may be used. Such carbon source as glucose, starch, organic acids etc., such nitrogen source as polypeptone, yeast extract, urea etc. and such trace element as vitamin, inorganic salts etc. may be suitably selected. Furthermore, it is effective to add corn steep liquor or distillers solubles to the medium. Especially, the distillers solubles may be used advantageously because it can be a perfect culture medium without adding any other components. Culture is carried out with aeration of 0.5 to 2.0 l/l, minute to about 25° C. for about 2 weeks. Cultured broth thus obtained is subjected to centrifugation to obtain the mycelium, followed by extracting with hot water. The extract is braught to 70% saturation with ethanol and the mixture allowed to stand overnight in a cold room. Precipitates thus obtained are dissolved in water and equal volume of water-saturated phenol is added to the solution. The mixture is vigorously skaken in cold and separated centrifugally to obtain water layer. This procedure is repeated twice. The water layers thus obtained are combined together, and then washed with ethyl ether to remove the residual phenol. Four volumes of pure ethanol is added to the water layer. The precipitate thus obtained is dissolved in 0.01 M Tris-HCl buffer (pH 6.95) and applied to an Ecteolacellulose column. The column is eluted with said buffer. Fractions showing the interferon inducing activity are collected, and after dialyzing and lyophilizing, a white amorphous powder is obtained.

The powder is dissolved in 0.01 M sodium acetate buffer (pH 4.0), applied on an equilibrated CM-cellulose column and eluted with said buffer. The eluted fraction showing an interferon inducing activity is collected, dialyzed and applied on an equilibrated Sephadex G-100 column (5 cm × 60 cm), followed by eluting with 0.3 M acetic acid containing 0.3 M NaCl. The fraction corresponding to peak A in FIG. 5 is collected, dialyzed, and lyophilized to yield white amorphous powder which is designated as KS-2-B.

The obtained KS-2-B may be parenterally, orally or rectally administered in powders, granules, tablets, capsules, suppositories, oils, solutions, emulsions and so forth.

Experimental Examples and Example of the present invention are shown.

EXPERIMENTAL EXAMPLE 1

DD1 mice with average body weight of 20 g (6 weeks in age) were intraperitoneally administered with 200 mg/kg of KS-2-B and 24 hours later, the animal was sacrificed to remove the blood. The blood was centrifuged at 3,000 r.p.m. for 10 minutes to obtain serum.

Titer of interferon was measured with the thymidinekinase less strain of mouse L-1D cell and vesicular stomatitis virus (VSV). The titer was obtained by definite protection of viral cytopathic effect (CPE) caused by the diluted blood serum. Indicated titer of interferon was calibrated by referring to International Unit of interferon provided by the National Institute of Health of U.S.A.

The results are shown in Table I.

TABLE I

| Substance administered | Intraperitoneal dose (mg/kg) | Interferon titer (International Unit)/ml serum |
| --- | --- | --- |
| KS-2-B | 200 | 2400 |

EXPERIMENTAL EXAMPLE 2

DD1 mice with body weight ranging from 14 to 16 g were infected intranasally with influenza virus and were administered intraperitoneally with KS-2-B according to three kinds of the schedules shown in Table II. The survival days and survival percentage of mice were compared with those of untreated mice. As the virus, mouse-adapted strain of influenza $A_2$/Kumamoto/$Y_5(H_2N_2)$ virus was challenged at 20 $LD_{50}$ dose. KS-2-B was administered each time at a dose of 141 mg/kg in saline.

The results are summarized in Table II.

TABLE II

| Treatment schedule with KS-2-B | Number of mice | Average of survival days | Survival percentage (%) |
| --- | --- | --- | --- |
| 2 and 1 days before infection | 10 | >20.3 | 50 |
| 1,2,3,4 and 5 days after infection | 10 | >22.0 | 60 |
| 2,3,4,5 and 6 days after infection | 10 | >16.2 | 30 |
| Untreated (saline) | 39 | 9.4 | 0 |

EXPERIMENTAL EXAMPLE 3

DD1 female mice with average body weight of 20 g (6 weeks in age) were administered intraperitoneally with 5 to 425 mg/kg of KS-2-B. Twenty four hours later, these mice were infected with *Listeria monocytogenesis* isolated from patient with Listerial infection. The infection was carried out by injecting 0.1 ml of a saline suspension of $10^8$ cells/ml into the tail vein of the mice. Survival percentage of mice was observed after 20 days between the treated and untreated groups.

The results are shown in Table III.

TABLE III

| Dose of KS-2-B (mg/kg) | Number of mice | Number of survivors after 20 days | Survival percentage (%) |
| --- | --- | --- | --- |
| 425 | 14 | 14 | 100 |
| 141 | 14 | 14 | 100 |
| 47 | 16 | 16 | 100 |
| 16 | 16 | 16 | 100 |
| 5 | 16 | 16 | 100 |
| 0 (Untreated) | 38 | 9 | 23.7 |

EXPERIMENTAL EXAMPLE 4

Both normal fibroblast cells derived from C3H mouse embryo and their SV-40 transformed cells were used as the target cells for testing the action of macrophage derived from KS-2-B treated mouse.

DD1 mice with average body weight of 20 g (6 weeks in age) were administered with 200 mg/kg of KS-2-B intraperitoneally and 24 hours later, the peritoneal exudate cells were washed out with serum-free RPM1-1640 medium. The washed exudate cells were spread over the petri dish (Falcon, 3.5 cm in diameter) and cultured in a $CO_2$ incubator for 2 hours. Thereafter, nonadherent cells were discarded and the adherent cells were washed two or three times with RPMI-1640 medium warmed up to 37° C. The cells adhered persistently to the petri dish were regarded as the macrophage derived from KS-2-B treated mouse. The activity was examined with the macrophage.

Meanwhile, the macrophage derived from non-KS-2-B treated mouse was obtained similarly.

Each macrophage was adjusted to $5 \times 10^5$ cells per a petri dish. The fibroblast cells or transformed cells mentioned earlier were added to each of the petri dishes containing the tested macrophages at the rate of $5 \times 10^4$ cells per $cm^2$ of the petri dish and subsequently cultured at 37° C. for 48 hours in $aOxCO_2$ incubator. Thereafter, the petri dish was thoroughly washed with phosphate buffer, fixed with methanol and subjected to Giemsa staining, followed by microscopic observation.

As the results, it was observed that the SV-40 transformed cells, when treated with the macrophage derived from KS-2-B treated mice, were killed and most of the residual cells disappeared, while when treated with the macrophage derived from non-KS-2-B treated mice, the transformed cells continued to propagate and no cell killing by macrophages was observed. On the other hand, normal fibroblast cells propagated normally on the macrophage derived from KS-2-B treated mice as well as on that from non-treated mice.

EXAMPLE

*Lentinus edodes* KSLE 28 (FERM-P No. 4196) was cultured preliminarily in 1 l of medium containing only distillers solubles at 24° C. for 14 days by shaking, and the resultant culture broth was inoculated into 10 l of the distillers solubles diluted to a specific gravity of 1.012 to 1.020 and cultured at 24° C. with aeration (1.8 l/l, minute) for 11 days. The resultant broth was then subjected to centrifugation, thereby 80 g of mycelium was obtained.

The mycelium was mixed with 10 l of hot 5% NaCl solution, and the mixture was boiled for 60 minutes, followed by centrifugation to separate into supernatant and residual mycelium. The residual mycelium was treated further two times in a similar manner to that described above. Ethanol was added to the combined supernatant to give a final alcohol concentration of 70% and allowed to stand overnight in a cold dark room. The precipitate thus obtained was dissolved in water, and an equal volume of water-saturated phenol was added to the solution. The mixture was shaken at cold temperature and then centrifuged to obtain the water layer. This procedure was repeated twice. The water layers obtained in this way were combined together, and then washed with ethyl ether to remove residual phenol. Residual ether in the water layer was removed by flushing with $N_2$ gas. Four volumes of pure ethanol was added to the resultant water layer and the mixture was allowed to stand overnight in a cold dark room.

The precipitate thus obtained was dissolved in 0.01 M Tris-HCl buffer (pH 6.95), and the resultant solution was applied to a Ecteola-cellulose column bufferized with said buffer. The column was eluted with said buffer and the eluate showing the interferon inducing activity was collected. After dialysing and lyophilizing, 1.5 g of a white powder was obtained.

The powder was dissolved in 0.01 M sodium acetate buffer (pH 4.0) and applied on a CM-cellulose column (2.6 × 36 cm), then eluted with said buffer. The eluate showing the interferon inducing activity was collected, dialyzed and concentrated. The concentrate was applied on a Sephadex G-100 column (5 × 60 cm) equilibrated with 0.3 M acetic acid containing 0.3 M sodium chloride and then eluted with said eluent. The eluate corresponding to the peak A in FIG. 5 was collected, dialyzed and then lyophilized to yield 0.3 g of KS-2-B finally.

What is claimed is:

1. KS-2-B having the following physicochemical properties:
   (1) Elemental analysis: C: 43.98%, H: 6.77%, N: 1.37%, Ash: trace
   (2) Molecular weight: 75,000 ± 15,000 (by ultrafiltration method)
   (3) Appearance: White amorphous powder
   (4) Decomposition point: Approx. 185° C.
   (5) UV spectrum As shown in FIG. 1.
   (6) IR spectrum As shown in FIG. 2.
   (7) pH: 5.92 (in aqueous solution)
   (8) Solubility: Soluble in water, insoluble in organic solvents such as ethanol, acetone, n-hexane, n-butanol, phenol and so forth
   (9) Specific optical rotation: $[\alpha]_D^{25} = +61.8°$ (0.788% aqueous solution)
   (10) Homogeneity: a. Homogeneous in equilibrium density gradient centrifugation (120,000 g × 72 hours, CsCl) b. Homogeneous in electrophoresis on cellulose acetate c. Homogeneous in gel filtration using "Sephadex G-100"
   (11) Specific gravity: $\rho = 1.623$ by equilibrium density gradient centrifugation (120,000 G × 72 hours, CsCl)
   (12) Color reaction:
      Phenol-$H_2SO_4$ reaction: positive
      Anthrone reaction: positive
      Molisch's reaction: positive
      Elson-Morgan reaction: negative
      Carbazole-$H_2SO_4$ reaction: positive
      Folin-Ciocarteau reaction: positive
      Biuret reaction: positive
      Toluidine blue O staining: negative
      Ninhydrin reaction: positive
   (13) Sugar composition: It is almost mannose
   (14) Amino acid composition: It is mainly serine, thereonine and alanine, and minutely glutamic acid, valine, proline, aspartic acid, glycine and isoleucine. Furthermore, although other amino acids are found in a very small quantity from time to time, histidine, arginine, cystine and methionine are absent
   (15) Linkage mode of mannan: From a result of enzymatic digestion with α-mannosidase, this substance is estimated to contain α-linked mannan in the molecule.

2. A method for manufacturing KS-2-B in accordance with claim 1 comprising culturing a strain selected from a group consisting of *Daedalea dickinsii* KSDD 6 (FERM-P No. 3993), *Lentinus edodes* KSLE 7 (FERM-P No. 3994) and *Lentinus edodes* KSLE 28 (FERM-P No. 4196) in a medium consisting essentially of distillers solubles under aerobic conditions until a substantial amount of KS-2-B is accumulated in the culture broth.

3. A composition for inducing interferon production in the body comprising an interferon increasing effective amount of KS-2-B in accordance with claim 1 as active component, and a pharmaceutically acceptable carrier.

4. A method for increasing the interferon of a patient comprising administering to said patient an interferon increasing effective amount of KS-2-B as defined in claim 1.

* * * * *